(12) United States Patent
Sasaki et al.

(10) Patent No.: US 7,531,160 B2
(45) Date of Patent: May 12, 2009

(54) FINE HOLLOW POWDER, THIN FLAKY TITANIUM OXIDE POWDER OBTAINED BY PULVERIZATION OF THE FINE HOLLOW POWDER AND PROCESSES FOR PRODUCING THE SAME

(75) Inventors: Takayoshi Sasaki, Tsukuba (JP); Mamoru Watanabe, Tsukuba (JP); Yuichi Michiue, Tsukuba (JP); Masaki Iida, Yokkaichi (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 11/802,897

(22) Filed: May 25, 2007

(65) Prior Publication Data
US 2008/0003176 A1 Jan. 3, 2008

Related U.S. Application Data

(62) Division of application No. 09/516,176, filed on Mar. 1, 2000.

(30) Foreign Application Priority Data

| Sep. 2, 1997 | (JP) | 9-254266 |
| Sep. 2, 1997 | (JP) | 9-254267 |
| Sep. 2, 1997 | (JP) | 9-254268 |
| Dec. 18, 1997 | (JP) | 9-364908 |
| Dec. 18, 1997 | (JP) | 9-364909 |
| Jan. 27, 1998 | (JP) | 10-030541 |
| Jan. 27, 1998 | (JP) | 10-030542 |

(51) Int. Cl.
*C01G 23/00* (2006.01)
*C01G 57/00* (2006.01)
*C01D 1/02* (2006.01)

(52) U.S. Cl. .................. 423/598; 423/593.1

(58) Field of Classification Search .......... 423/579, 423/592.1, 593.1, 598
See application file for complete search history.

(56) References Cited

U.S. PATENT DOCUMENTS 3,325,242 A 6/1967 von Bichowsky (Continued)

FOREIGN PATENT DOCUMENTS

EP 0501505 A2 9/1992

(Continued)

OTHER PUBLICATIONS

English Translation of Groult et al. "New Oxides with Leaf-Like Structure: Non Stoichiometric Potassium Titanates $Kx(MyTi2-y)O4$" Journal of Solid State Chemistry 32 (1980) 289-296.*

(Continued)

*Primary Examiner*—Steven Bos
*Assistant Examiner*—Anthony J Zimmer
(74) *Attorney, Agent, or Firm*—Paul E. White; Manelli Denison & Selter, PLLC

(57) ABSTRACT

The present invention relates to fine hollow powder with a titanium oxide shell, obtained by spray drying an exfoliated titania sol, and thin flaky titanium oxide powder obtained by pulverizing the fine hollow powder, and also to processes for producing the same. The present fine hollow powder and thin flaky titanium oxide powder have a distinguished dispersibility and are useful for additives to cosmetics, pigments, paints, etc., and the present fine hollow powder also has a distinguished flowability and is useful for seed particles for flow measurement.

3 Claims, 11 Drawing Sheets

U.S. PATENT DOCUMENTS

| | | | |
|---|---|---|---|
| 3,331,658 A | 7/1967 | Lewis et al. | |
| 3,347,798 A | 10/1967 | Baer et al. | |
| 3,395,203 A | 7/1968 | Morita | |
| 4,087,581 A | 5/1978 | Vincent et al. | |
| 4,192,691 A | 3/1980 | Armanini | |
| 4,349,456 A | 9/1982 | Sowman | |
| 4,448,599 A | 5/1984 | Mackenzie et al. | |
| 4,450,184 A | 5/1984 | Longo et al. | |
| 4,546,090 A | 10/1985 | Olson et al. | |
| 4,564,556 A | 1/1986 | Lange | |
| 4,985,380 A | 1/1991 | Douden | |
| 5,397,759 A | 3/1995 | Torobin | |
| 5,427,771 A | 6/1995 | Grollier et al. | |
| 5,492,870 A | 2/1996 | Wilcox et al. | |
| 5,656,716 A * | 8/1997 | Schmidt et al. | 528/279 |
| 5,858,078 A | 1/1999 | Andes et al. | |
| 5,863,514 A | 1/1999 | Sasaki et al. | |
| 6,004,525 A | 12/1999 | Tani et al. | |
| 6,440,383 B1 | 8/2002 | Duyvesteyn et al. | |
| 6,752,973 B2 | 6/2004 | Okusako | |

FOREIGN PATENT DOCUMENTS

| | | |
|---|---|---|
| EP | 0601594 A1 | 6/1994 |
| EP | 0918045 | 5/1999 |
| JP | 58-223606 | 12/1983 |
| JP | 61118311 A | 6/1986 |
| JP | 61161212 | 7/1986 |
| JP | 5-154374 | 6/1993 |
| JP | 6-124491 | 5/1994 |
| JP | 122518 | 5/1994 |
| JP | 6-285358 | 10/1994 |
| JP | 06-285358 A | 11/1994 |
| JP | 9-25123 | 1/1997 |
| JP | 9132514 | 5/1997 |
| JP | 09 067124 | 7/1997 |
| JP | 09227122 A | 9/1997 |
| WO | WO 97/30952 | 2/1997 |

OTHER PUBLICATIONS

Groult et al.,"Nouveaux oxides a structure en feuillets: Les titanates de potassium non-stoechiometriques Kx(MyTi2-y)O4" J. Solid State Chemistry 32, pp. 289-296 (1980).

* cited by examiner

×1,000

×6,000

×60,000

×1,500

×60,000

FINE HOLLOW POWDER, THIN FLAKY TITANIUM OXIDE POWDER OBTAINED BY PULVERIZATION OF THE FINE HOLLOW POWDER AND PROCESSES FOR PRODUCING THE SAME

This is a divisional application of U.S. application Ser. No. 09/516,176 filed Mar. 1, 2000.

TECHNICAL FIELD

The present invention relates to fine hollow powder in a novel form with an titanium oxide shell, which is useful for additives to pigments, paints, cosmetics, coating agents, resin such as nylon, etc. or white paper, photofunctional materials such as catalysts, etc., and ultraviolet shielding materials and a process for producing the fine hollow powder; thin flaky titanium oxide powder obtained by pulverization of the fine hollow powder and a process for producing the thin flaky titanium oxide powder; cosmetics comprising the fine hollow powder or the thin flaky titanium oxide powder; and seed particles for flow measurement, which comprise the fine hollow powder.

Still furthermore, the present invention relates to a commercially advantageous process for providing an exfoliated titania sol necessary for the production of the fine hollow powder.

BACKGROUND ART

Fine titanium oxide powder in various forms such as granular, acicular, dendritic, flaky and other forms, has been so far known except for the hollow forms.

The fine hollow powder according to the present invention can be obtained by spray drying a laminated titania sol, as will be described later.

So far known processes for producing the laminated titania sol include a process, which comprises mixing cesium oxide or a compound decomposable to cesium oxide by heating with titanium oxide, followed by heating, treating the resulting layered cesium titanate with an aqueous acid solution, thereby replacing the interlayer cesium ions with protons (whose existing forms are hydronium ions), and mixing the resulting titanic acid powder with an aqueous solution of ammonium compound or amine compound under stirring (JP-A-9-25123). However, the process suffers from a low reactivity of the cesium titanate with the aqueous acid solution and a long time, for example, at least 3 days, in the replacement of the cesium ions with the protons (whose existing forms are hydronium ions) (JP-A-6-122518), and is very inefficient and costly in the commercial production.

Layered alkali metal titanate compounds with parts of host framework $Ti^{4+}$ sites being vacant or replaced with divalent or trivalent alkaline earth metal ions or transition metal ions, such as said cesium titanate [for example, as disclosed in I. E. Grey, I. C. Madsen and J. A. Watts, J. Solid State Chem. 66, 7 (1987), D. Groult, C. Mercey and B. Raveau, J. Solid State Chem. 32, 289 (1980), etc.] can only serve to exchange their interlayer ions, with the result of an insufficient ion exchangeability and inefficient production of exfoliated titania sol.

The well known process for producing thin flaky titanium oxide particles comprises freeze drying an exfoliated titania sol (JP-A-9-67124). However, the process requires freeze drying of a dilute exfoliated titania sol to obtain fine powder with a distinguished dispersibility. That is, freezing of a relatively large amount of water is inevitable before vacuum drying and thus an enormous amount of energy must be consumed, causing an economical problem.

DISCLOSURE OF INVENTION

The present invention is directed to fine hollow powder with a titanium oxide shell and a distinguished dispersibility also to a process for commercially and economically advantageously producing thin flaky titanium oxide powder with a distinguished dispersibility.

As a result of extensive studies to solve the problems, the present inventors have found that fine titanium oxide powder in a special form so far not available and with a distinguished dispersibility can be unexpectedly obtained by spray drying an exfoliated titania sol. Further, thin flaky titanium oxide powder with an equivalent dispersibility to that obtained by the conventional process comprising freeze drying an exfoliated titania sol can be commercially and economically produced by pulverizing the fine titanium oxide powder in the special form.

Furthermore, the present inventors have found that an exfoliated titania sol useful for the production of the present fine hollow powder can be commercially advantageously provided by mixing two different kinds of alkali metal oxides with titanium dioxide in a specific ratio, followed by heating, treating the resulting mixed alkali metal titanate with an aqueous acid solution, thereby replacing alkali metal ions of the mixed alkali metal salt with protons (whose existing forms are hydronium ions) to obtain a layered titanic acid compound, and then dispersing the layered titanic acid compound in a liquid medium in the presence of a basic compound, and have established the present invention.

Therefore, an object of the present invention is to provide fine hollow powder with a titanium oxide shell. Another object of the present invention is to provide a process for producing thin flaky titanium oxide powder, characterized by pulverizing the fine hollow powder. Other objects of the present invention will be clarified by the detailed description which follows.

"Titanium oxide" as herein referred to includes anhydrous titanium oxide, hydrated titanium oxide, hydrous titanium oxide, etc.

BEST MODE FOR CARRYING OUT THE INVENTION

Fine Hollow Powder

The present invention relates to fine hollow powder with a titanium oxide shell.

"Fine hollow powder" herein referred to means fine powder with a shell enclosing the inside space of the particle and includes, for example, powder in a balloon form, a pingpong ball form, etc. It is not always necessary that the shell enclose the inside space completely, but even such incomplete fine hollow powder with a partly cracked or defected shell or inclusion therein of thin flaky titanium oxide powder resulting from pulverization of the fine hollow powder can serve the purpose without any problem. Furthermore, inclusion therein of impurities originating from raw materials or deposition thereof on the shell has no problem either, so far as it gives no adverse effect on such uses as will be described later.

For the sizes of the fine hollow powder, the outer diameter is preferably 0.1-5,000 μm and the shell thickness is preferably 1nm-100 μm.

Particularly in application to cosmetics, the outer diameter (D) is preferably 1-5,000 μm, more preferably 10-500 μm and the shell thickness (T) is preferably 1nm-100 μm, more preferably 10nm -100 nm, from the viewpoints of dispersibility and smoothness to the touch.

In application to a fluidity-donating agent, etc., the thinner the shell relative to the outer diameter, the smaller the apparent specific gravity and the better the fluidity donatability as desired. In application to adsorbents, photocatalysts, etc., not the inside space but the surface can contribute to the reaction. Thus, the thinner the shell relative to the outer diameter, the larger the available surface area as desired. In these cases, a ratio of outer diameter (D) to shell thickness (T), i.e. D/T, is desirably in a range of 50-5,000.

For the fine hollow powder, it is no matter whether a surface treatment has been carried out by the so far well known method or not. The surface treatment includes, for example, silicone treatment, lecithin treatment, resin treatment, tackifier treatment, silane treatment, fluorocompound treatment, inorganic oxide treatment, ultraviolet absorbent treatment, polyhydric alcohol treatment, amino acid treatment, coloring matter treatment, soap treatment, oil treatment, wax treatment, pendant-formation treatment, etc. Particularly, fluorocompound treatment using a perfluoroalkyl phosphate ester is preferable. The surface treatment can be carried out by any of dry, wet and gas phase processes. It is also possible to combine a plurality of surface treatment together, for example, by a combination of a treatment of fine follow powder with a volatile, reactive silicone and a successive addition of alkylyl chains, polyoxyalkylene groups or the like to the resulting powder, thereby conducting a pendant formation treatment to make the powder hydrophilic or lipophilic.

Figure 1:
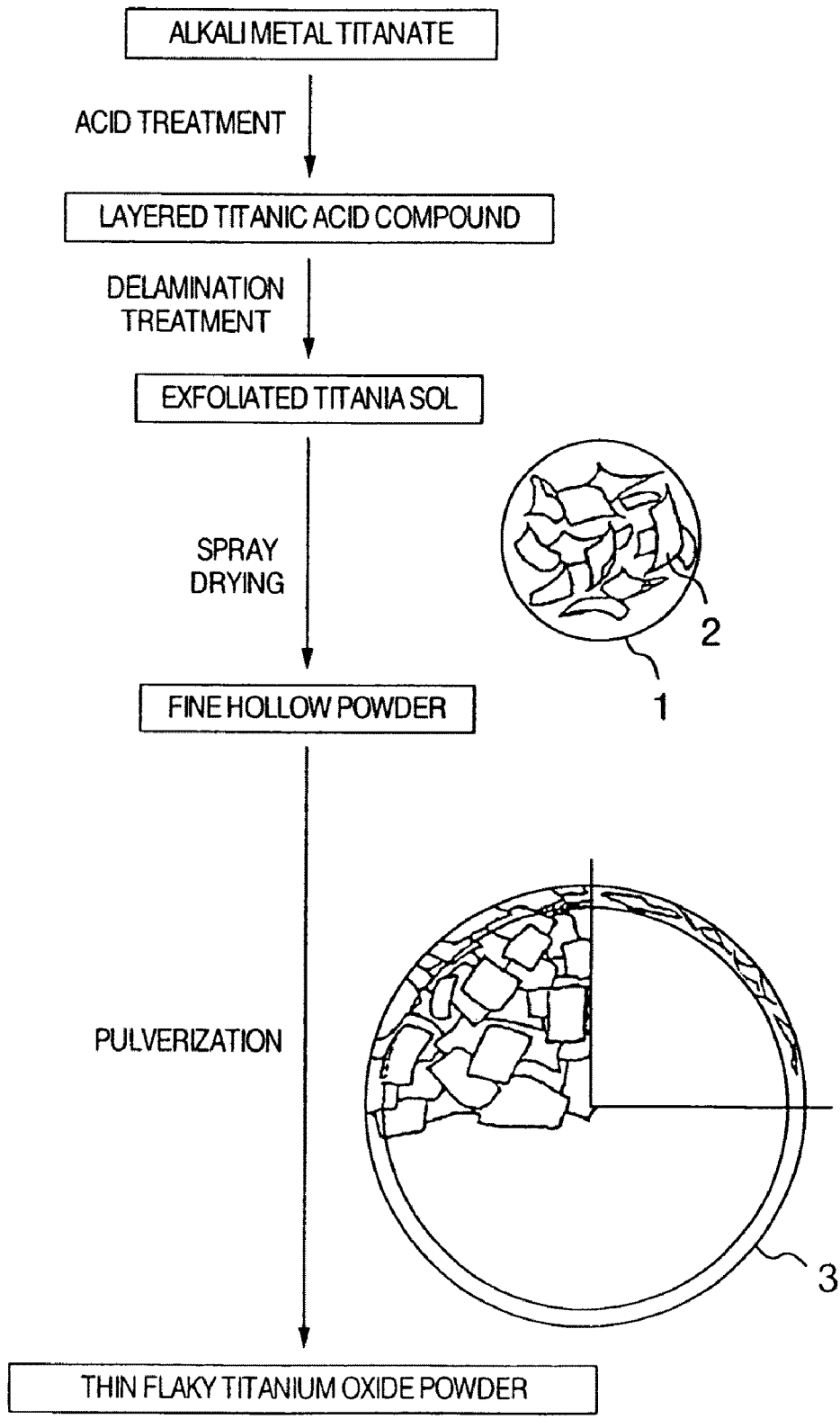
FIG. 1 is a schematic view showing one embodiment of steps of producing fine hollow powder and thin flaky titanium oxide powder.

In the present invention, the fine hollow powder can be produced by spray drying an exfoliated titania sol, and its formation mechanism can be presumed as follows. As shown in FIG. 1, the sprayed laminated titania sol takes the form of fine liquid droplets 1, which are immediately thereafter exposed to high temperatures for drying. Evaporation of water takes place not only on the surfaces of the liquid droplets, but also in the inside space due to rapid heating of the liquid droplets as whole, causing to inflate as balloons and dry at the same time. Thus, laminated particles 2 are stuck with one another to form a fine hollow powder 3 having an outer diameter of 0.1-5,000 μm.

The spraying method applicable to the spray drying includes, for example, a disc type, a pressure atomizer type, a twin-fluid atomizer type, etc. The disc type is a method comprising feeding a solution onto a disc under high speed rotation and spraying the solution into fine droplets by centrifuge. According to this method, fine droplets of a desired size can be obtained by changing revolutions per minute of the disc according to the viscosity, feed rate, etc. of the solution, even if they are largely changed. Applicable viscosity of the solution is in a range of 1 to several ten thousand cP and the disc type is widely used for small test types as well as mass production types.

The pressure atomizer type is a method comprising pumping the solution under high pressure and atomizing it through nozzles with such characteristics as easy maintenance and applicability suitable for mass production atomizers. Applicable viscosity of the solution is in a range of 1 to several thousand cP.

The twin-fluid atomizer type is a method comprising ejecting the solution together with compressed air or steam, thereby atomizing it in a fine droplet form, and is a system suitable for small size atomizers and also for the treatment of a solution of low viscosity because of imperative passage through as relatively small nozzles as those of the pressure atomizer type.

In the present invention, any of the foregoing types can produce satisfactory liquid droplets of exfoliated titania sol as a precursor upon proper selection of the conditions. However, the disc type is commercially most preferable, because it can treat even a sol of high concentration and high viscosity and also is suitable for mass production.

As already mentioned above, the sprayed liquid droplets are dried by immediate contact with hot air. Temperature of hot air is in a range of preferably 100°-800° C., more preferably 150°-400° C. So long as the hot air is within said temperature range, a satisfactory and less defectable hollow form can be easily obtained by sufficient evaporation of water from the liquid droplet inside.

It is preferable to further heat treatment of the spray dried fine hollow powder by a band drier, a microwave drier, an electric oven, a fluidized bed calcinating kiln, etc., depending upon the uses. Heat treatment temperature is preferably in a range of 100°-800° C. The heat treatment is directed to crystallization of titanium oxide, removal of residual water, removal of residual basic compounds and improvement of light fastness. So long as the heat treatment is carried out in said temperature range, said objects of the heat treatment can be fully attained with less defectable hollow form.

Exfoliated Titania Sol

Exfoliated titania sol for the spray drying must have a viscosity of preferably 5-10,000 cP, more preferably 100-3,000 cP.

Sizes of exfoliated titania particles for the sol are preferably 0.5-100 nm in thickness and 0.1-30 μm in both width and length, more preferably 0.5-10 nm in thickness and 1-10 μm in both width and length. In case of ultimately obtaining thin flaky titanium oxide powder as will be described later, the thickness is in a range, of preferably 0.5-50 nm, more preferably 0.5-1 nm. So long as the exfoliated titania particles for the sol are in said thickness range, the sol can have an appropriate stickiness without blasting of the resulting hollow powder even in the course from the spraying to the drying. So long as the width and length are within said ranges, the sol can be easily sprayed with easy hollow formation.

Dispersing medium applicable to the exfoliated titania sol includes water and organic solvents such as methanol, acetonitrile, etc., but water is most preferable from the economical viewpoint.

Preferable concentration of exfoliated titania sol for spray drying is in a range of 0.5-20% by weight. So long as the concentration is within said range, spraying can be easily carried out and fine hollow powder with a shell of appropriate thickness can be obtained. That is, the powder can be easily pulverized into a flaky form. The concentration within said range is economically advantageous and suitable for the commercial production.

The laminated titania sol can be produced by mixing an alkali metal oxide or a compound decomposable to an alkali metal oxide by heating with titanium oxide or a compound capable of forming titanium oxide by heating, followed by heating, treating the resulting alkali metal titanate with an aqueous acid solution, thereby forming titanic acid compounds in a layered structure, and then dispersing and delaminating the layered titanic acid compounds in a liquid medium in the presence of a basic compound.

For the alkali metal oxide, at least one of oxides of lithium, sodium, potassium, rubidium and cesium can be used. For the compound decomposable to an alkali metal oxide by heating, carbonates, hydroxides, nitrates, sulfates, etc. of alkali metals can be used, but above all the carbonates and the hydroxides are preferable. The compound capable of forming titanium oxide by heating includes, for example, hydrous titanium oxides such as metatitanic acid, orthotitanic acid, etc., and organic titanium compounds such as titanium alkoxides, etc., where hydrous titanium oxides are preferable.

The basic compound includes, for example, alkylamines such as propylamine, diethylamine, etc., quaternary ammonium hydroxides such as tetramethylammonium hydroxide, tetraethylammonium hydroxide, tetrapropylammonium hydroxide, tetrabutylammonium hydroxide, etc., and alkanolamines such as ethanolamine, aminomethylpropanol, etc., where quaternary ammonium hydroxides and alkanolamines are preferable. The amount of basic compound to be added is preferably 0.5-10 equivalent weights, more preferably 1-2 equivalent weights on the basis of the layered titanic acid compound. Under experimentally selected optimum conditions for the kind and amount of basic compound to be added, the layered titanic acid compounds are completely delaminated one by one to form a sol of single laminated titania particles (two-dimensional sheets), while keeping the dispersion stability. If the kind and amount of basic compound are not optimum, the basic compound and water may be taken into interlayer spaces to leave largely swollen (osmotically swollen) layered titanic acid compounds without complete delamination. Incomplete delamination has no problem, so long as it is within a practically acceptable range.

Novel Exfoliated Titania Sol

In the present invention an exfoliated titania sol particularly comprising delaminated particles represented by the following composition formula:

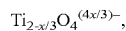

where x is 0.57-1.0, specifically by the following composition formula:

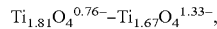

as dispersed, can be used.

Exfoliated titania sols comprising thin flaky particles represented by the following composition formula:

where x is 0.60-0.75, as dispersed, have been so far known, but the present exfoliated titania sol has a novel composition, where the negative charge of titanate ions is larger than that of the conventional ones and thus the adsorbability of basic compound is higher and dispersion into the liquid medium is faster.

The exfoliated titania particles for constituting the present novel sol form a two-dimensional structure due to linkage by edge sharing of $TiO_6$ octahedrons further with 9.5-17% of $Ti^{4+}$ sites being vacant, resulting in a large negative charge of the exfoliated particles. Size of the particles can be set as desired, depending upon the uses, but is usually 0.5-1 nm in thickness and 0.1-30 μm in both width and length.

The present novel sol can be produced from the following novel mixed alkali metal titanate as a starting material in the same manner as mentioned above.

Novel Mixed Alkali Metal Titanate

Mixed alkali metal titanate for use in the production of said novel sol can be produced specifically in the following manner. Alkali metal oxides $M_2O$ and $M'_2O$, where M and M' represent mutually different kinds of alkali metals, or compounds decomposable to $M_2O$ and $M'_2O$, respectively, by heating are mixed with titanium dioxide or a compound capable of forming titanium dioxide by heating in a molar ratio of M/M'/Ti of 3/1/5-3/1/11 and then the mixture is heated at a temperature of 500°-1,100° C., preferably 600°-900° C. To conduct reaction sufficiently to reduce the amounts of unreacted raw materials and suppress formation of materials of other compositions, said temperature range is desirable.

The mixed alkali metal titanate so produced is a compound of novel composition in a layer structure of orthorhombic crystal, represented by the following composition formula:

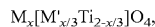

where M and M' represent mutually different kinds of alkali metals and x is 0.50-1.0, with parts of host framework $Ti^{4+}$ sites being replaced with a different kind of alkali metal ions from that of interlayer alkali metal ions.

The alkali metal ions represented by M and M' in the compound are active and have an exchange reactivity with other cations or cause inclusion of organic compounds by intercalation. Thus, treated with an aqueous acid solution causes to exchange interlayer alkali metal ions (M) and host framework alkali metal ions (M') with protons (whose existing forms are hydronium ions) for a short time, thereby producing an exfoliated titania sol efficiently at a low production cost in case of commercial production.

Value for the suffix x of the composition formula can be controlled by changing the mixing ratio of starting materials. To obtain a uniform single phase compound, it is preferable to conduct the mixing sufficiently in the synthesis steps, for example, to mix the starting materials under grinding in an automatic mortar, etc. Compounds with various particle sizes can be obtained by appropriately changing the heating conditions.

The mixed alkali metal titanate has a higher reactivity with an aqueous acid solution and a faster exchange reaction with protons than those of intermediate products obtained by the conventional process, for example, cesium titanate. To obtain layered titanic acid compounds by exchanging the cesium ions of the conventional cesium titanate with protons (whose existing forms are hydronium ions), it is necessary to treat 1 g of cesium titanate with 100 cm³ of 1 N hydrochloric acid at room temperature for 3 days, whereas to exchange cesium ions and lithium ions of the present compound, where M=Cs and M'=Li, with protons (whose existing forms are hydronium ions), it is necessary to treat 1 g of the powder of said compound with 100 cm³ of 1 N hydrochloric acid at room temperature only for one day.

Figure 2:
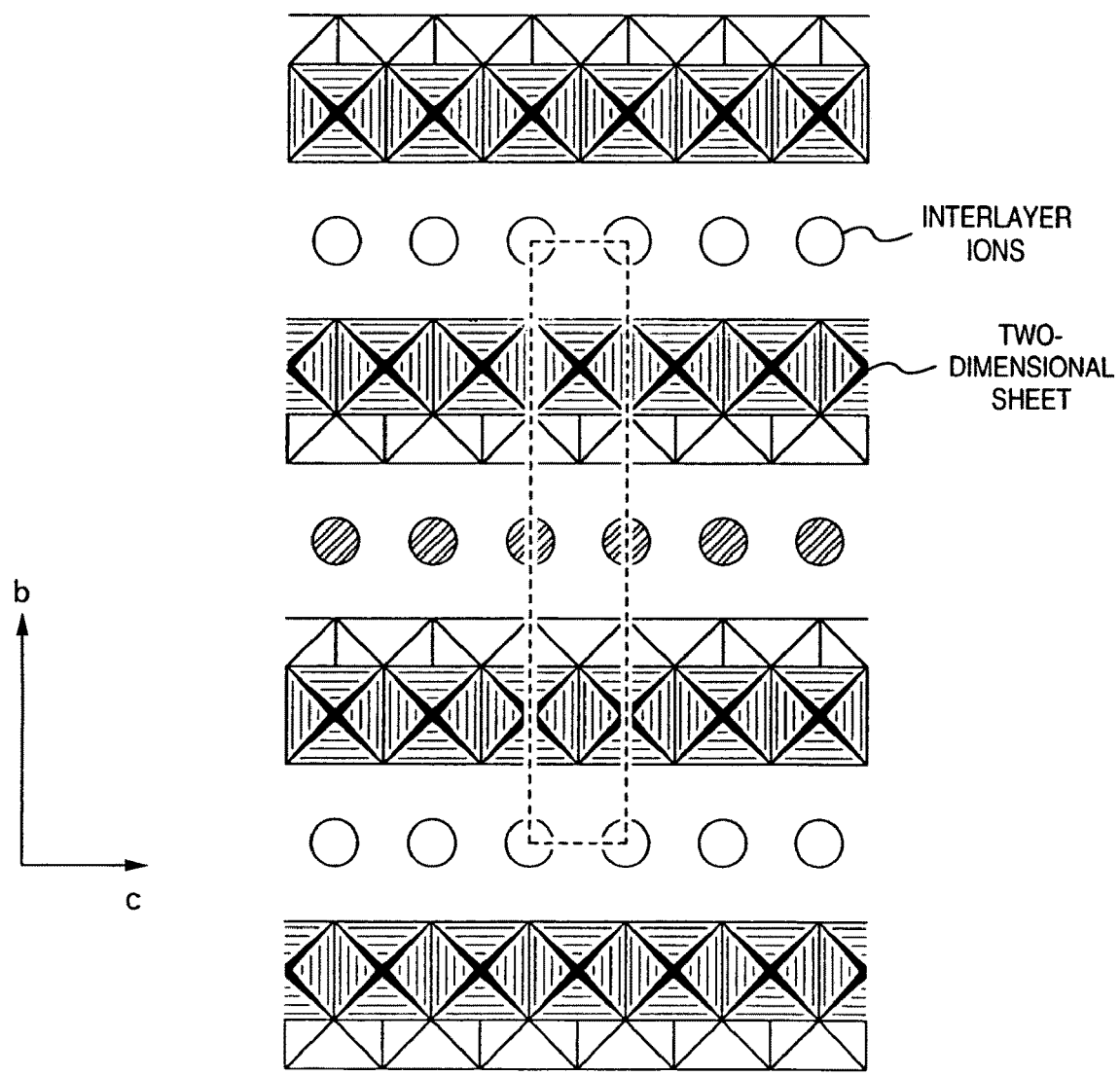
FIG. 2 is a projection view of the present mixed alkali metal titanate, relative to the (100) plane in a crystal structure where the alkali metal M has an ionic size of not larger than that of potassium, and the area surrounded by the dotted line corresponds to a unit cell.
Figure 3:
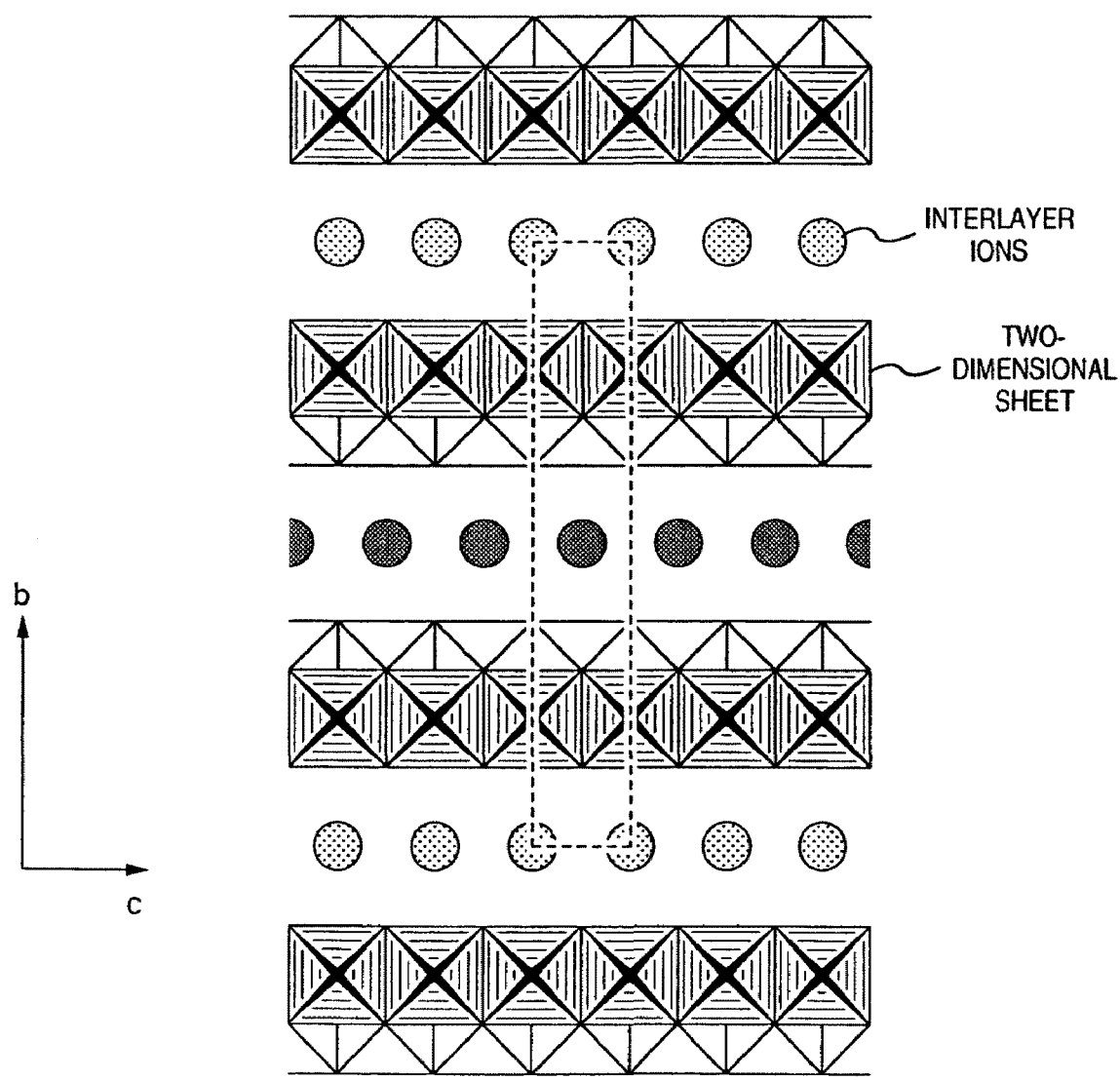
FIG. 3 is a projection view of the present mixed alkali metal titanate, relative to the (100) plane, in a crystal structure where the alkali metal M has an ionic size of not smaller than that of rubidium and the area surrounded by the dotted line corresponds to a unit cell.

The present mixed alkali metal titanate is in a layer structure as shown in FIG. 2 in case that the sizes of interlayer ions are not larger than those of potassium ions and in a layer structure as shown in FIG. 3 in case of not smaller than those of rubidium ions, while forming a two-dimensional sheet form by linkage due to edge sharing of $TiO_6$ octahedra, and takes an orthorhombic crystal form containing alkali metal ions between the sheets. Crystallographic composition of the two-dimensional sheets comprises $TiO_2$ which is properly electrically neutral, but is negatively charged because 8-17% of $Ti^{4+}$ octahedral sites are replaced with different kind of alkali metal ions from that of the interlayer alkali metal ions. Interlayer alkali ions are to compensate for the negative charging.

The space group of the novel compound is Cmcm in case that the sizes of the interlayer ions are not larger than those of potassium ions and Immm in case of not smaller than those of rubidium ions. Crystallographical data, though dependent upon the kind of interlayer alkali metal ions and the amount of exchanged alkali metal ions at the host framework Ti sites, are shown for a typical composition, i.e. case of M=K, M'=Li and x=0.8 in Table 1 on the powder X-ray diffraction data and in Table 2 on the result of Rietveld analysis.

TABLE 1

X-ray diffraction data of the present mixed alkali metal titanate

| h | k | l | d calc (Å) | d obs (Å) |
|---|---|---|---|---|
| 0 | 2 | 0 | 7.77 | 7.76 |
| 0 | 4 | 0 | 3.88 | 3.88 |
| 1 | 1 | 0 | 3.71 | 3.71 |
| 1 | 3 | 0 | 3.076 | 3.077 |
| 0 | 2 | 1 | 2.777 | 2.777 |
| 0 | 6 | 0 | 2.589 | 2.590 |
| 1 | 5 | 0 | 2.411 | 2.412 |
| 0 | 4 | 1 | 2.361 | 2.361 |
| 1 | 1 | 1 | 2.321 | 2.320 |
| 1 | 3 | 1 | 2.138 | 2.137 |
| 0 | 6 | 1 | 1.952 | 1.952 |
| 2 | 0 | 0 | 1.912 | 1.912 |
| 1 | 5 | 1 | 1.873 | 1.872 |
| 2 | 2 | 0 | 1.857 | 1.857 |

Lattice constants are: a=3.8244(3)Å, b=15.534(1)Å, c=2.9733(1)Å, and V=176.72(1)Å³; the unit cell contains two composition formula compounds; and the calculated density is 3.387 g/cm³.

TABLE 2

Results of Rietveld analysis of the present mixed alkali metal titanate

| Atom | g | x | y | z | B |
|---|---|---|---|---|---|
| K | 0.4 | 0.5 | 0.4884 (6) | 0.75 | 7.9 (1) |
| Ti, Li | 1.0 | 0.0 | 0.316 (1) | 0.75 | 1.08 (6) |
| O1 | 1.0 | 0.0 | 0.2165 (2) | 0.25 | 1.2 (1) |
| O2 | 1.0 | 0.0 | 0.3870 (3) | 0.25 | 1.1 (1) | g: Occupancy
B: Temperature parameter
$R_{wp} = 0.1194$,
$R_p = 0.0936$,
$R_e = 0.0339$,
$R_I = 0.0412$,
$R_F = 0.0279$ Preferable combinations of M and M' for the production of the present exfoliated titania sol are as follows:

(M, M')=(K, Li), (Rb, Li) and (Cs, Li)

Layered Titanic Acid Compound

As already described above, layered titanic acid compounds can be formed by treating an alkali metal titanate with an aqueous acid solution.

The aqueous acid solution includes, for example, aqueous solutions of an inorganic acid such as hydrochloric acid, sulfuric acid, etc. and an organic acid such as acetic acid, oxalic acid, etc., but is not particularly limited. Concentration is preferably 0.5-6 N, more preferably 1-3 N. To allow an appropriate time for the reaction and also prevent decomposition of titanic acid, said concentration range is desirable.

To efficiently conduct the reaction with acid, it is preferable to use a method comprising preparing an acidic slurry of alkali metal titanate and then converting the slurry to a cake by a filter press or an aspiration filter such as Buechner funnel, etc., while passing fresh acid through the cake under aspiration. After the contact and reaction with the aqueous acid solution, it is desirable to remove excess acid therefrom by washing with deionized water, etc. Removal of excess acid ensures a good stability for the viscosity, dispersibility, etc. in the finished sol.

Novel Layered Titanic Acid Compound

In the present invention, a compound of novel composition in a layer structure of orthorhombic crystal represented by the following composition formula:

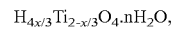

$$H_{4x/3}Ti_{2-x/3}O_4 \cdot nH_2O,$$

where x is 0.5-1.0 and n is 0-2, with the interlayer alkali metal ions being replaced with hydrogen ions and parts of the host framework $Ti^{4+}$ sites being replaced with protons can be used as said layered titanic acid compound.

Titanic acid compounds with interlayer protons (whose existing forms are hydronium ions) and water molecules have been so far known, but the present composition is novel. Interlayer protons and host framework protons of the compound (the existing forms of protons being hydronium ions) are active and can reversibly cause exchange reaction with other cations or intercalation of organic compounds.

Its structure corresponds to that of FIG. 3, i.e. orthorhombic crystal structure with two-dimensional sheets formed by linkage by edge sharing of $TiO_6$ octahedrous and with protons (whose existing forms are hydronium ions) existing between the sheets. Crystallographic composition of the two-dimensional sheet is $TiO_2$, which is properly electrically neutral but is negatively charged because 8-17% of $Ti^{4+}$ octahedral sites are vacant. The interlayer protons (whose existing forms are hydronium ions) are to compensate for the negative charging.

In the present layered titanic acid compound, not only the interlayer protons (whose existing forms are hydronium ions) and the protons (whose existing forms are hydronium ions) exchanged for the host framework alkali metal ions in the mixed alkali metal titanate as the starting material are in a mobile state, and thus the amount of the active ions in the compound is larger than that of the conventional compound.

Therefore, the present novel layered titanic acid compound is well expected to serve as adsorbents, ion exchange materials, catalysts, separating materials, treating materials for noxious chemicals.

Crystallographic data of the present layered titanic acid compound, though dependent upon the amount of vacant host framework $Ti^{4+}$ sites, are shown in Table 3 on the powder X-ray diffraction data of a typical composition, e.g. case of x=0.8 and n=1.0.

TABLE 3

X-ray diffraction data of the present layered titanic acid compound

| h | k | l | d calc (Å) | d obs (Å) |
|---|---|---|---|---|
| 0 | 2 | 0 | 9.19 | 9.21 |
| 0 | 4 | 0 | 4.59 | 4.60 |
| 1 | 1 | 0 | 3.71 | 3.71 |
| 1 | 3 | 0 | 3.219 | 3.219 |
| 0 | 6 | 0 | 3.062 | 3.062 |
| 0 | 3 | 1 | 2.693 | 2.693 |
| 1 | 5 | 0 | 2.636 | 2.636 |
| 1 | 0 | 1 | 2.350 | 2.351 |
| 0 | 5 | 1 | 2.323 | 2.323 |
| 1 | 2 | 1 | 2.277 | 2.277 |
| 1 | 4 | 1 | 2.092 | 2.092 |
| 0 | 7 | 1 | 1.975 | 1.975 |
| 2 | 0 | 0 | 1.892 | 1.892 |
| 1 | 6 | 1 | 1.864 | 1.864 |
| 2 | 2 | 0 | 1.853 | 1.854 |

Lattice constants are as follows: a=3.7836(3)Å, b=18.371(2)Å, c=2.9984(2)Å, and V=208.42(2)Å$^3$; the unit cell contains two composition formula compounds; and the calculated density is 2.359 g/cm$^3$.

The present novel layered titanic acid compound can be produced from said novel mixed alkali metal titanate as a starting material in the same manner as above.

Thin Flaky Titanium Oxide Powder

Said laminated titania sol can be used as a starting material for the present fine hollow powder, as already described before, and pulverization of the fine hollow powder can give thin flaky titanium oxide powder as pulverization fragments. Pulverization cannot always disintegrate the powder even to sizes of original exfoliated titania particles, but gives aggregates of several to several tens of layers of exfoliated titania particles as stacked one upon another. The higher the intensity of pulverization, the smaller the width and length of thin flaky titanium oxide powder. Particle shapes of the resulting thin flaky titanium oxide powder can be controlled by the intensity of pulverization. To obtain thin flaky titanium oxide powder, it is desirable to use a pulverizer of relatively low pulverization intensity such as Colloplex mill, etc.

Sizes of the thin flaky titanium oxide powder are preferably 1-100 nm in thickness and 0.1-500 μm in both width and length, and, particularly for an ultraviolet shielding materials for cosmetics, are 20-80 nm in thickness and 1-500 μm in both width and length. So long as the thickness is kept within said range, ultraviolet rays can be well absorbed, while keeping good transparency. So long as the width and length are kept within said range, the extendability on the skin is distinguished without giving any roughness to touch.

The present thin flaky titanium oxide powder can serve well with or without any conventional well known surface treatment as in the case of the fine hollow powder as described before. The surface treatment can be carried out after the spray drying of the exfoliated titania sol or after the pulverization or at the same time as the pulverization.

It is desirable to heat treat the thin flaky titanium oxide powder before and/or after the pulverization, preferably before the pulverization, depending upon uses, as in the case of the fine hollow powder. Heat treatment, when carried out before the pulverization, can prevent reaggregation or deposition onto the pulverizer during the pulverization due to decrease in the water content. Heat treatment temperature is preferably in a range of 100°-800° C. When kept within said temperature range, the desired object of heat treatment can be attained and the thin shape is less defected at increasing temperatures.

Uses

Fine hollow powder with a titanium oxide shell and thin flaky titanium oxide powder so produced in said processes have a much distinguished dispersibility with less secondary aggregation.

The present fine hollow powder and thin flaky titanium oxide powder can be applied for additives to various pigments, cosmetics, paints, coating materials, resins, white paper and photofunctional materials such as catalysts, etc. as an ultraviolet shielding material, a fluidity-donating material, an adsorbent, a photocatalyst and coloring matter.

Particularly, the fine hollow powder can be utilized as an ultraviolet shielding material, an adsorbent and a photocatalyst due to the presence of the titanium oxide shell. Furthermore, the apparent specific gravity is very low and the flowability and heat insulatability are distinguished due to the presence of vacant inside space, and thus the fine hollow powder can be utilized as seed particles for flow measurement systems, fluidity donating materials, or for light weight cement and mortar, light weight heat-insulating materials, architectural repairing putty, heat-resistant coating putty, explosive sensitization, paper molding, reflecting material, plastic filler, adhesive, master model, syntactic foam, synthetic lumber, artificial marble and boring. Furthermore, light interference can take place when the shell thickness is controlled to submicron-nanometer levels and thus the fine hollow powder can be utilized as coloring matter.

The present fine hollow powder, when utilized for cosmetics, can be used in various form such as a lotion form, a cream form, a paste form, a stick form, an emulsion form, etc. upon mixing with, e.g. oil components, humectants, surfactants, pigments, perfumes, antiseptics, water, alcohols, thickeners, etc. When the shell thickness of the fine hollow particles is controlled to submicron size or less in actual application to cosmetics upon mixing, the shell can be crushed to thin flaky titanium oxide powder by rubbing the cosmetics on the skin by fingers, thereby increasing the retainability on the skin effectively.

When the fine hollow powder or thin flaky titanium oxide powder is used as an additive to paints or coating materials, the spray drying temperature is particularly preferably in a range of 150°-250° C. When the spraying is carried out within said temperature range, the basic compound remains in the powder without any change and facilitates dispersion when added to paints or coating materials.

Flow measurement system using the present hollow powder as seed particles is of such a type of irradiating seed particles existing in a fluid with light and detecting the scattered light, thereby measuring a fluid flow, and includes, for example, a laser Doppler velocimeter, a particle image velocimeter, etc. The present fine hollow powder has a vacant inside space and thus a low apparent specific gravity and a distinguished follow-up to the fluid flow. Furthermore, it comprises titanium oxide of high refractive index and thus has a distinguished light scatterability. That is, the present fine hollow powder ensures flow measurement with a high accuracy. Seed particles for the flow measurement system preferably have an outer diameter of 5-50 μm and a shell thickness of 10-100 nm from the viewpoints of follow-up to the fluid flow and light scatterability.

The present exfoliated titania sol is useful for the production of fine hollow powder or thin flaky titanium oxide powder, and has expected uses in coating materials and catalyst by itself. Novel mixed alkali metal titanate or layered titanic acid compound provided according to the present invention has a distinguished ability to exchange metal ions or protons (whose existing forms are hydronium ions) with inorganic or organic cations or take up organic compounds by intercalation, and thus is used not only as a starting material or an intermediate product for the fine hollow powder or thin flaky titanium oxide powder, but also has expected uses in adsorbent, ion exchange materials, catalysts, separating materials, treating materials for noxious compounds, electrode materials and dielectric materials by itself.

EXAMPLES

The present invention will be described in detail below, referring to Examples, but the present invention is not limited thereto.

Example 1

Synthesis of Mixed Alkali Metal Titanate

Potassium carbonate ($K_2CO_3$), lithium carbonate ($Li_2CO_3$) and titanium dioxide ($TiO_2$) were mixed together in a molar ratio of K/Li/Ti=3/1/6.5 and fully ground. Then, the mixture was placed in a platinum crucible and heated at 800° C. for 5 hours, whereby white powder was obtained (Sample A).

Elemental analysis of the powder revealed that the molar ratio of K/Li/Ti was kept at 3/1/6.5. X-ray diffraction pattern determination revealed that C-base-centered orthorhombic lattices could be exponentially expressed, and results of Rietveld analysis revealed that the powder was lepidocrocite type, layered mixed alkali metal titanate represented by the following composition formula:

$$K_x[Li_{x/3}Ti_{2-x/3}]O_4,$$

where x=0.8.

Sample A was molded into coin-shaped pellets by a handy press, followed by heating at 800° C. for one hour. Sizes of heated pellets were 6.99 mm in diameter and 0.99 mm in thickness, and the weight was 0.1324 g. Ionic conductivity at 200° C. of the pellets was determined by a complex impedance method and found to be $4.0 \times 10^{-8}$ Scm$^{-1}$. That is, the present mixed alkali metal titanate was found useful for electroconductive applications such as electrode materials, etc.

Furthermore, 1.0 g of Sample A was dispersed in 100 ml of zinc amine complex containing 100 ppm of zinc as $Zn^{2+}$, followed by stirring for one hour and removal of Sample A by filtration, and $Zn^{2+}$ concentration of the filtrate was determined by an atomic absorption spectrometry and was found that the original $Zn^{2+}$ concentration was reduced to 30 ppm. That is, the present mixed alkali metal titanate was found useful for ion exchange materials, separating materials and treating materials for organic compounds.

Example 2

Synthesis of Mixed Alkali Metal Titanate

Cesium carbonate ($Cs_2CO_3$), lithium carbonate ($Li_2Co_3$) and titanium dioxide ($TiO_2$) were mixed together in a molar ratio of Cs/Li/Ti=3/1/7.57 and fully ground. The mixture was placed in a platinum crucible and heated at 900° C. for 5 hours, whereby white powder was obtained. The white powder was identified by powder X-ray diffractometry in the same manner as in Example 1 and found to be lepidocrocite type, layered alkali metal titanate represented by the following composition formula:

$$Cs_x[Li_{x/3}Ti_{2-x/3}]O_4,$$

where x=0.7 (Sample B).

Sample B was molded into coin-shaped pellets by a handy press, followed by heating at 800° C. for one hour. Sizes of the heated pellets were 6.99 mm in diameter and 0.99 mm in thickness, and the weight was 0.1324 g. Ionic conductivity at 200° C. of the pellets was determined by a complex impedance method and found to be $1.4 \times 10^{-8}$ Scm$^{-1}$.

Example 3

Synthesis of Mixed Alkali Metal Titanate

Potassium hydroxide (KOH), lithium hydroxide (LiOH) and titanium dioxide ($TiO_2$) were mixed together in a molar ratio of K/Li/Ti=3/1/6.5 and fully ground. The mixture was placed in a platinum crucible and heated at 600° C. for 5 hours, whereby white powder was obtained. The white powder was identified by powder X-ray diffractometry in the same manner as in Example 1 and found to be a mixture of lepidocrocite type, layered mixed alkali metal titanate represented by the following composition formula:

$$K_x[Li_{x/3}Ti_{2-x/3}]O_4,$$

where x=0.8, and a small amount of residual titanium oxide (Sample C).

Example 4

Synthesis of Layered Titanic Acid Compound

One gram of Sample A obtained in Example 1 was leached in 100 cm³ of 1 N hydrochloric acid at room temperature with stirring for one day to conduct reaction therebetween, followed by filtration, water washing and drying, whereby layered titanic acid compound powder was obtained (Sample D).

Sample D was subjected to fluorescent X-ray spectrometry and found that the lithium content and the potassium content were reduced to one thousandth or less (less than the detection limit) and one hundredth, respectively, of the original contents before the contact with hydrochloric acid and that substantially all the alkali metal ions were replaced with protons.

Furthermore, 1.0 g of Sample D was dispersed in 100 ml of zinc amine complex containing 100 ppm zinc as $Zn^{2+}$, followed by stirring for one hour and removal of Sample D by filtration. $Zn^{2+}$ concentration of the filtrate was determined by filtration. $Zn^{2+}$ concentration of the filtrate was determined by atomic absorption spectrometry and found that the original $Zn^{2+}$ concentration was reduced to 59 ppm. That is, the present mixed alkali metal titanate was found useful for ion exchange materials, separating materials and treating materials for organic compounds.

Example 5

Synthesis of Layered Titanic Acid Compound

One gram of Sample B obtained in Example 2 was leached in 100 cm³ of 1 N hydrochloric acid at room temperature with stirring for one day to conduct reaction therebetween, followed by filtration, water washing and drying, whereby the present layered titanic acid compound powder was obtained (Sample E).

Example 6

Synthesis of Layered Titanic Acid Compound

One gram of Sample C obtained in Example 3 was leached in 100 cm³ of 1 N hydrochloric acid at room temperature with stirring for one day to conduct reaction therebetween, followed by filtration, water washing and drying, whereby the present layered titanic acid compound powder was obtained (Sample F).

Samples E and F were subjected to the same analysis as for Sample D and it was found that substantially all the alkali metal ions contained in the mixed alkali metal titanates as the starting materials were replaced with protons.

Example 7

Synthesis of Exfoliated Titania Sol

Six kilograms of layered titanic acid compound powder (Sample D) obtained in Example 4 was added to 0.1 m³ of an aqueous tetrabutylammonium hydroxide solution (concentration: 310 mol m⁻³), followed by shaking at about 150 rpm by a shaker for one day, whereby an exfoliated titania sol having a 5wt. % $TiO_2$ concentration and a viscosity of 510 cP was obtained (Sample G), where the viscosity was determined by a BL type viscometer.

No solid precipitate was observed in Sample G even after being left standing for a while.

Figure 4:
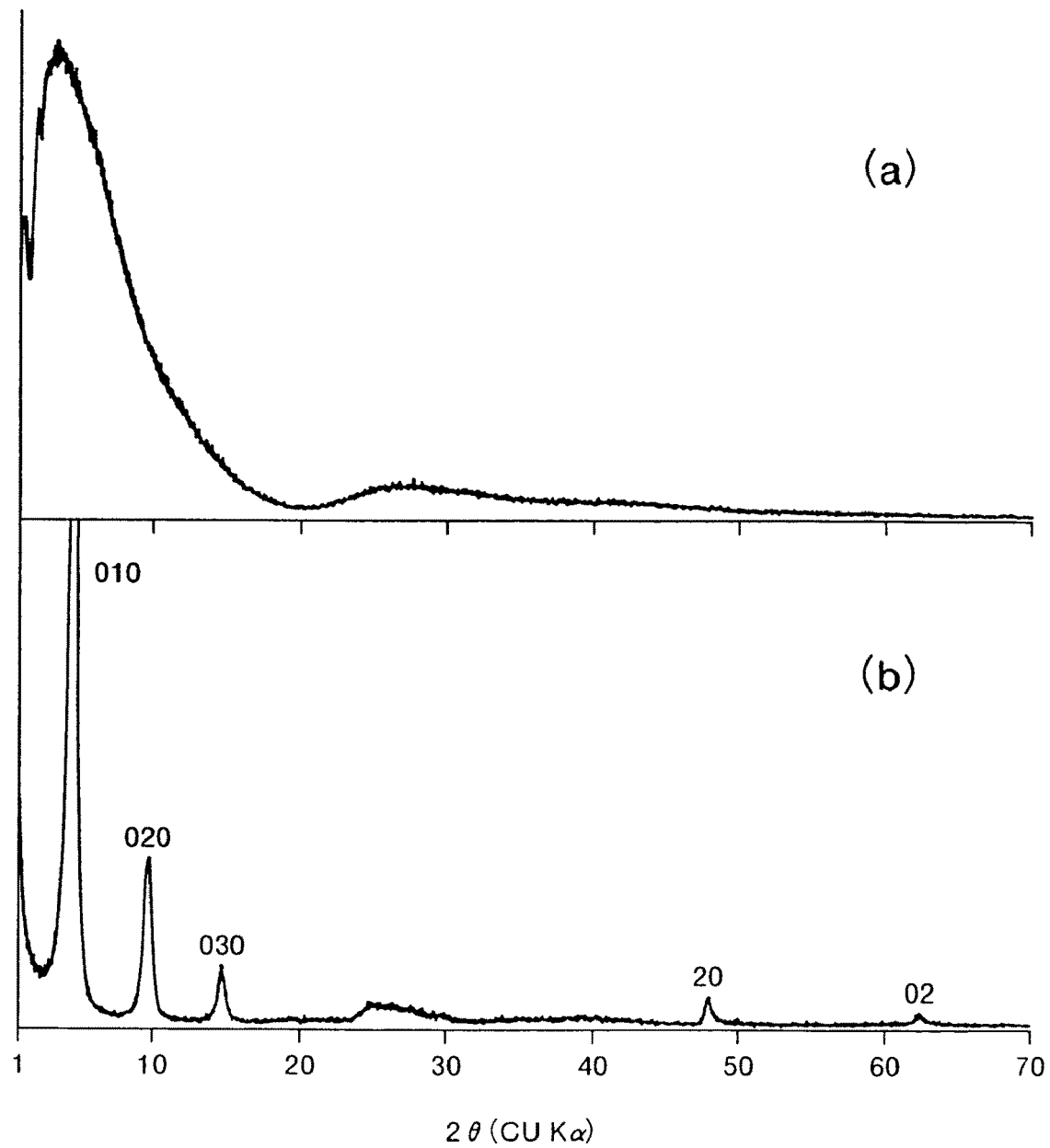
FIG. 4 is X-ray diffraction charts of a precipitate paste obtained by centrifuging a titania sol of Sample G right after the centrifuging (a) and after drying in air (b), respectively.

Sample G was separated into a substantially clear supernatant liquid and a paste-like precipitate by centrifuging at 15,000 rpm for 30 minutes. The precipitate was presumed to be aggregates of particles dispersed in the sol. FIG. 4(a) is an X-ray diffraction chart of the paste-like precipitate just after taking out of the centrifuge tube, showing an amorphous pattern without any diffraction peaks based on periodic atomic arrangements. After spontaneous drying, the dried paste-like precipitate, was subjected to X-ray diffractometry and a diffraction chart of FIG. 4(b) was obtained, where "20" and "02" bands due to the structure in the two-dimensional sheet were observed to show that the atomic arrangement was retained in the two-dimensional sheet and also a clear "0k0" (k=an integer) basal reflection series was observed to show that a plurality of the two-dimensional sheets were laid one upon another by drying. Taking these facts and observation of amorphous diffraction pattern of the paste-like precipitate into consideration, it would be reasonable to presume that the delaminated particles dispersed in the sol are composed of one-by-one delaminated two-dimensional sheets. Non-observation of "20" and "02" bands in FIG. 4(a) would be due to the so called preferred orientation, i.e. occurrence of parallel arrangement of two-dimensional sheets to a sample holder plate, which took place when Sample G is placed on the sample holder plate.

The two-dimensional sheet was represented by the following composition formula:

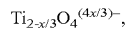

$$Ti_{2-x/3}O_4^{(4x/3)-},$$

where x=0.8, and the sheet thickness was estimated to be 0.75 nm by crystal structure analysis of the host layer.

Furthermore, Sample C was diluted and freeze dried, followed by scanning electron microscope observation, whereby delaminated particles, 1 μm wide and 1 μm long, were found.

Example 8

Synthesis of Exfoliated Titania Sol 0.5 g of Sample E obtained in Example 5 was added to 100 cm³ of an aqueous ethanolamine solution (concentration: 0.14 mol dm⁻³), followed by shaking at about 150 rpm by a shaker for one day, whereby a milky white sol with a sense of clearness was obtained (Sample H).

No solid precipitate was observed in Sample H even after being left standing for a while.

X-ray diffractometry and scanning electron microscope observation of Sample H were carried out in the same manner as for Sample G, and it was found that the sol was an exfoliated titania sol containing delaminated particles, 0.75 nm thick, 20 μm wide and 20 μm long, represented by the same composition formula as for Sample G as dispersed therein.

Example 9

Synthesis of Exfoliated Titania Sol 0.5 g of Sample F obtained in Example 6 was added to 100 cm³ of an aqueous tetrabutylammonium hydroxide solution (concentration: 0.16 mol dm⁻³), followed by shaking at about 150 rpm by a shaker for one day, whereby a milky white sol with a sense of clearness was obtained (Sample I).

Precipitate of fine white particles was slightly observed at the bottom in Sample I after being left standing for a while. Even further shaking by the shaker for two days failed to reduce the amount of the precipitate of fine white particles, and thus it was presumed the fine white particles were titanium oxide particles entrained from the starting material.

After Sample I was left standing for a while, the precipitate was removed therefrom by decantation, and then the sol was subjected to the same X-ray diffractometry and scanning electron microscope observation as for Sample G, and found to be an exfoliated titania sol containing delaminated particles, 0.75 nm thick and 0.1 μm wide, represented by the same composition formulas as for Sample G as dispersed therein.

Comparative Example 1

Synthesis of Exfoliated Titania Sol

Cesium carbonate ($Cs_2CO_3$) and titanium dioxide ($TiO_2$) were mixed together in a molar ratio of Cs/Ti=1/5.3, and fully ground. Then, the mixture was placed in a platinum crucible and heated at 800° C. for 40 hours, whereby white powder of alkali metal titanate represented by the following composition formula:

$$Cs_xTi_{2x/4}O_4,$$

where x=0.7, was obtained.

Then, 1 g of the white powder so obtained was leached in 100 cm³ of 1 N hydrochloric acid at room temperature with stirring for 3 days to conduct reaction therebetween. At the time of reaction after one day as well as after two days, replacement of cesium ions with protons was found not satisfactory. Then, after filtration, water washing and drying, layered titanic acid compound powder represented by the following composition formula:

$$H_xTi_{2-x/4}O_4 \cdot H_2O,$$

where x=0.7, was obtained.

Then, 0.5 g of the layered titanic acid compound powder was added to 100 cm³ of an aqueous tetrabutylammonium hydroxide solution (concentration: 0.1 mol dm⁻³), followed by shaking at about 150 rpm by a shaker for 3 days, whereby a milky white sol with a sense of clearness was obtained (Sample J).

No solid precipitate was observed in Sample J, even after being left standing for a while, but it was found at the time of shaking after one day as well as after two days that solid matters were precipitated by leaving it standing for a while, showing that the dispersion was not satisfactory.

Sample J was subjected to the same X-ray diffractometry and scanning electron microscope observation as for Sample G, and found to be an exfoliated titania sol containing delaminated particles, 0.75 nm thick, 0.1 μm wide and 0.1 μm long, represented by the above composition formula.

Example 10

Synthesis of Fine Hollow Powder

The exfoliated titania sol (Sample G) obtained in Example 7 was dried by a disc type spray drier (Model OC-25 made by ohgawara Kakoki K.K., Japan), where spraying was carried out by revolving a pin type disc at 24,000 rpm, and drying was carried out with hot air at 200° C., whereby the present fine hollow powder (Sample K) was obtained. It was found by scanning electron microscope observation that Sample K was fine hollow powder, about 20 μm in outer diameter, about 100 nm in shell thickness, in a ratio of outer diameter (D) to shell thickness (T), i.e. (D/T)=about 200.

Figure 5:
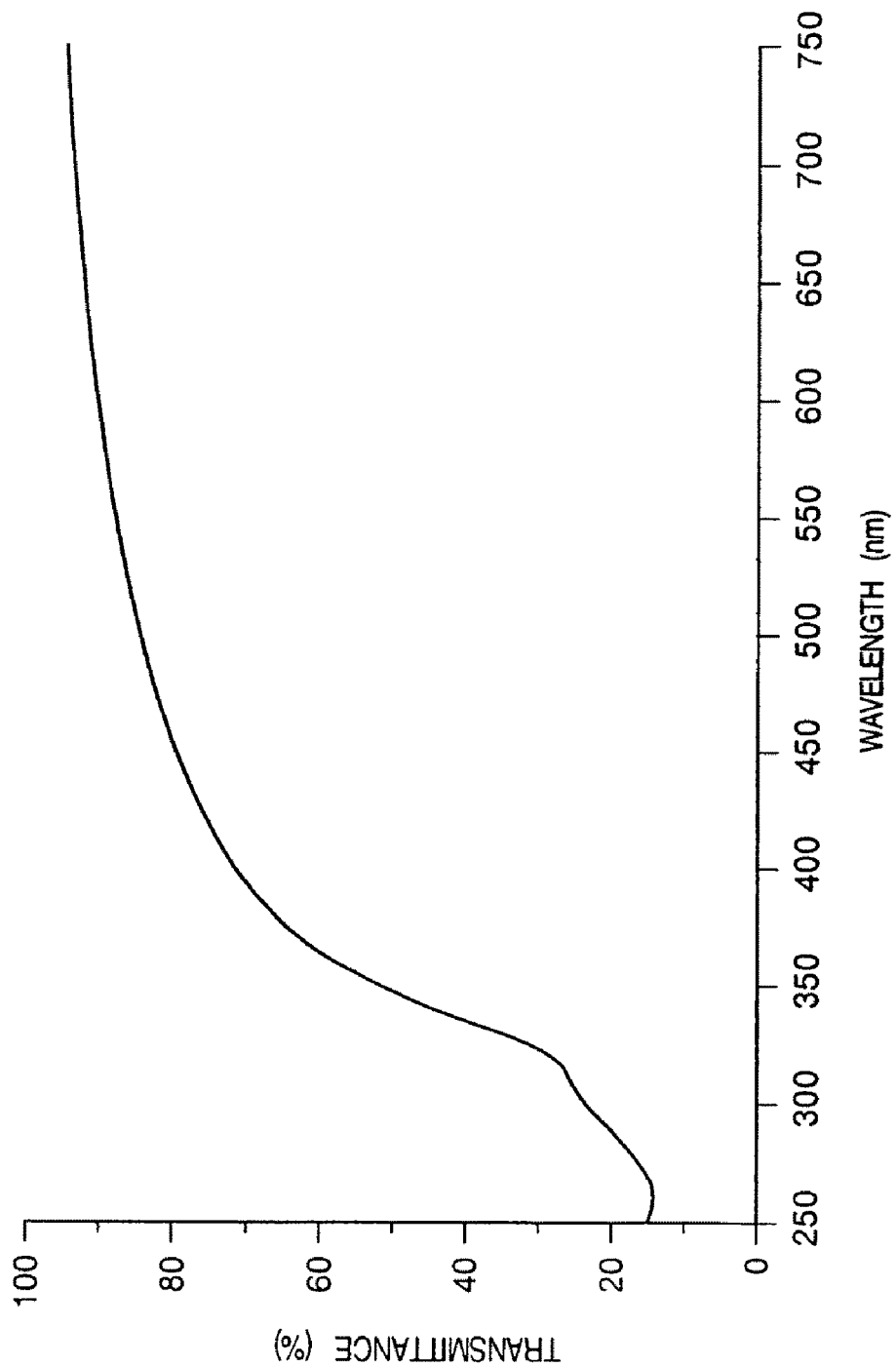
FIG. 5 is a spectrometric transmittance curve of a thin film using the present fine hollow powder (Sample K).

5 g of Sample K was suspended in 95 g of deionized water under ultrasonic dispersion for 10 minutes, and then 150 g of ethyl alcohol was further added thereto to prepare a coating material. The coating material was applied to a glass plate by a spin coater and heat treated at 650° C. for 20 minutes, whereby a thin transparent titanium oxide film was obtained. Spectroscopic transmittance curve of the thin titanium oxide film was determined and the results are shown in FIG. 5, showing a distinguished ultra-violet shieldability. When the thin titanium oxide film was irradiated with black light at 1 mW/cm², the contact angle of water was changed from 37° to 3.4°, showing an ultrahydrophilic property.

Example 11

Synthesis of Fine Hollow Powder

Sample K obtained in Example 10 was heat treated at 670° C. for one hour, whereby the present fine hollow powder was obtained (Sample L).

Figure 6:
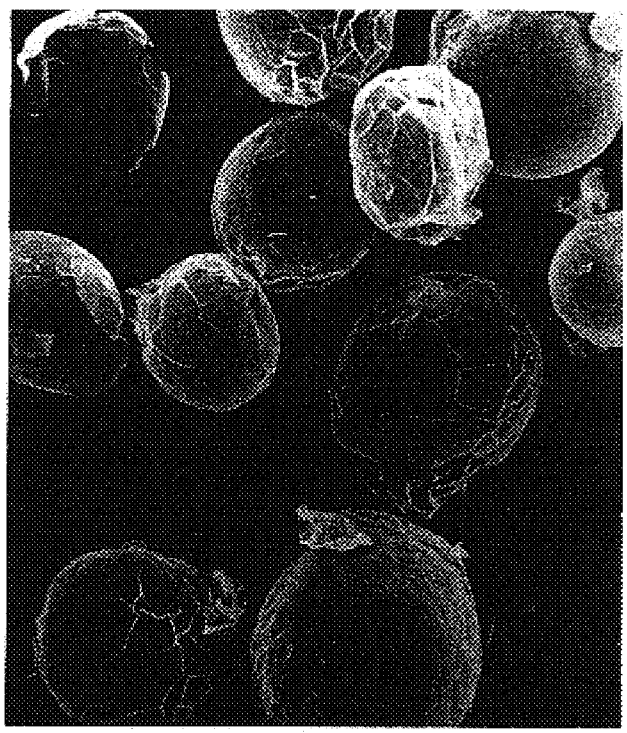
FIG. 6 is a scanning electron micrograph of the present fine hollow powder (Sample L) (magnification: ×1,000).
Figure 7:
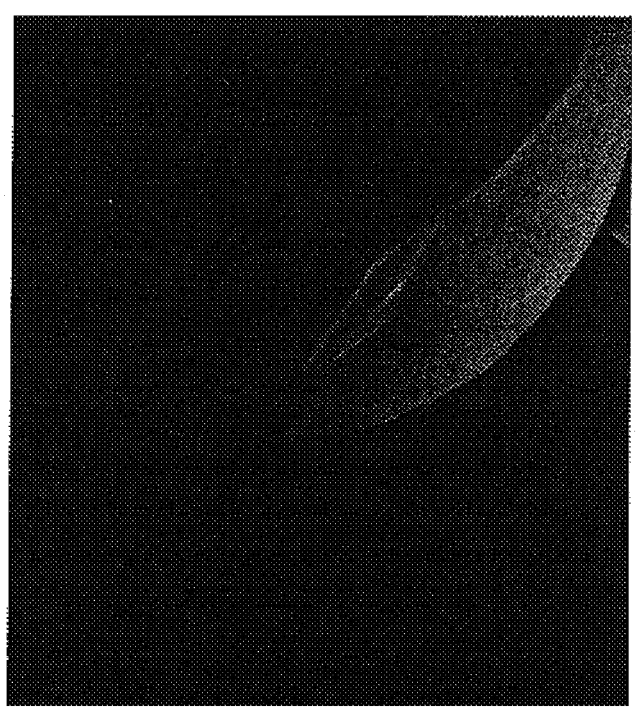
FIG. 7 is a scanning electron micrograph of crushed sample L by intentional pulverization (magnification: ×6,000).
Figure 8:
FIG. 8 is an enlarged scanning micrograph of the central part of FIG. 7 (magnification: ×60,000).

Scanning electron micrograph of Sample L is shown in FIG. 6 and scanning electron micrograph of crushed product obtained by intentionally crushing Sample L by a crusher is shown in FIG. 7. Enlarged scanning electron micrograph of the central part of FIG. 7 is shown in FIG. 8. It was found from FIGS. 6 and 8 that Sample L was fine hollow powder, about 20 μm in outer diameter and about 100 nm in shell thickness, in a ratio of outer diameter (D) to shell thickness (T), i.e. (D/T)=about 200.

Example 12

Preparation of Thin Flaky Titanium Oxide Powder

Sample K obtained in Example 10 was pulverized by Colloplex mill (Stud mill model 63Z made by IEC Co.)., whereby the present flaky titanium oxide powder was obtained (Sample M). It was found by scanning electron microscope observation that Sample M was flaky titanium oxide, about 30 nm in thickness and about 10 μm in width and length.

5 g of Sample M was suspended in 100 ml of deionized water under ultrasonic dispersion for 10 minutes to prepare a coating material. The coating material was applied to a glass plate by a spin coater and heat treated at 600° C. for one hour, whereby a thin transparent titanium oxide film was obtained.

Example 13

Preparation of Thin Flaky Titanium Oxide Powder

Fine hollow powder (Sample L) obtained in Example 11 was pulverized by Colloplex mill (made by Alpine Co.), whereby the present flaky titanium oxide powder was obtained (Sample N).

Figure 9:
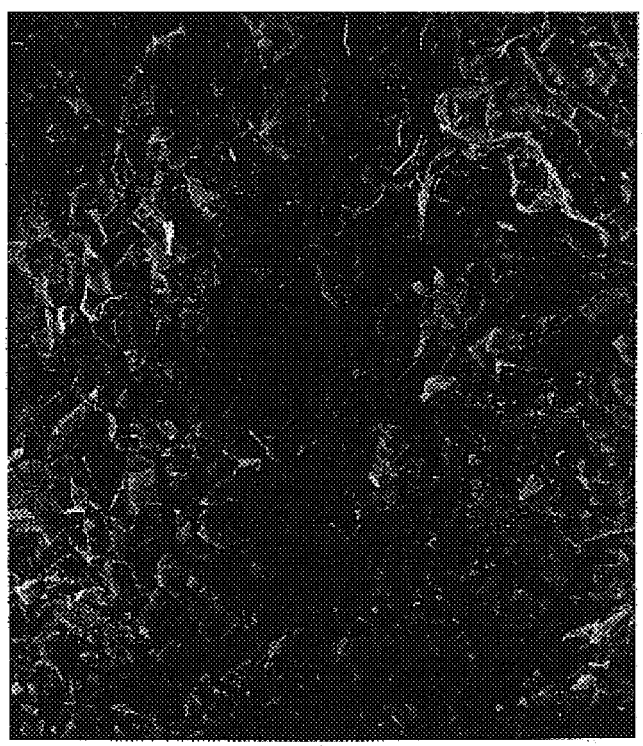
FIG. 9 is an electron micrograph of the present thin flaky titanium oxide powder (Sample N) (magnification: ×1,500).

Electron micrograph of Sample N is shown in FIG. 9. It was found from FIG. 9 that Sample G was flaky titanium oxide, about 30 nm in thickness and about 10 μm in width and length, as distributed substantially without any secondary aggregation.

Comparative Example 2

Preparation of Planar Titanium Oxide Powder

Exfoliated titania sol (Sample G) of Example 7 was placed in a crucible and dried and heat treated at 650° C. for one hour in an electric oven, and then pulverized by Colloplex mill (made by Alpine Co.), whereby titanium oxide powder was obtained (Sample O).

Figure 10:
FIG. 10 is an electron micrograph of planar titanium oxide powder obtained by heating an exfoliated titania sol (Sample O) (magnification: ×60,000).

Electron micrograph of Sample O is shown in FIG. 10. It was found from FIG. 10 that Sample O is composed of planar particles, about 300 nm in thickness.

Test Example 1

Samples L, N and O were finished into powdery foundations in the following formulation and procedure to obtain cosmetics l, n and o respectively.

| Formulation | % by weight |
|---|---|
| Talc | 15.0 |
| mica | 25.0 |
| kaolin | 5.0 |
| Sample | 38.0 |
| titanium dioxide | 2.0 |
| zinc stearate | 1.0 |

-continued

| Formulation | % by weight |
|---|---|
| poly(methyl methacrylate) powder | 3.0 |
| squalane | 5.0 |
| liquid paraffin | 1.0 |
| lanolin acetate | 1.0 |
| glycerine triisooctanate | 2.0 |
| octyldodecyl myristate | 2.0 |

Procedure

Components (1) to (7) were mixed together by a Henschel mixer, and then components (8) to (12) melted by heating at 70° C. were added thereto, followed by mixing in an automatic mortar fully and sieving through a screen.

Evaluation

Extendability and sense of clearness on the skin when actually applied to the skin were scored for the cosmetics l, n and o by 10 panelists on the 10-point basis. The more distinguished the extendability and the sense of clearness, the higher the scored point. Points scored by 10 panelists were averaged and the results are shown in Tables 4 and 5. That is, the fine hollow powder obtained according to the present invention were found to have distinguished extendability and sense of clearness on the skin when used as cosmetics.

TABLE 4

Results of evaluation of cosmetics containing fine hollow powder

|  | Cosmetics l |
|---|---|
| Extendability on skin | 10.0 |
| Sense of clearness on skin | 7.6 |

TABLE 5

Results of evaluation of fine laminated titanium oxide powder and planar titanium oxide powder

|  | Cosmetics n | Cosmetics o |
|---|---|---|
| Extendability on skin | 10.0 | 2.3 |
| Sense of clearness on skin | 8.3 | 2.1 |

Test Example 2

Figure 11:
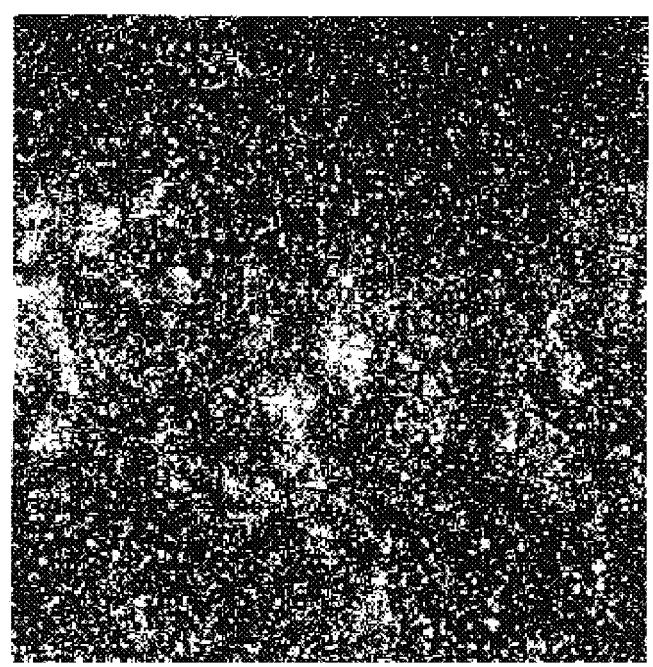
FIG. 11 is a light scattering image picture obtained with Sample L as seed particles.
Figure 12:
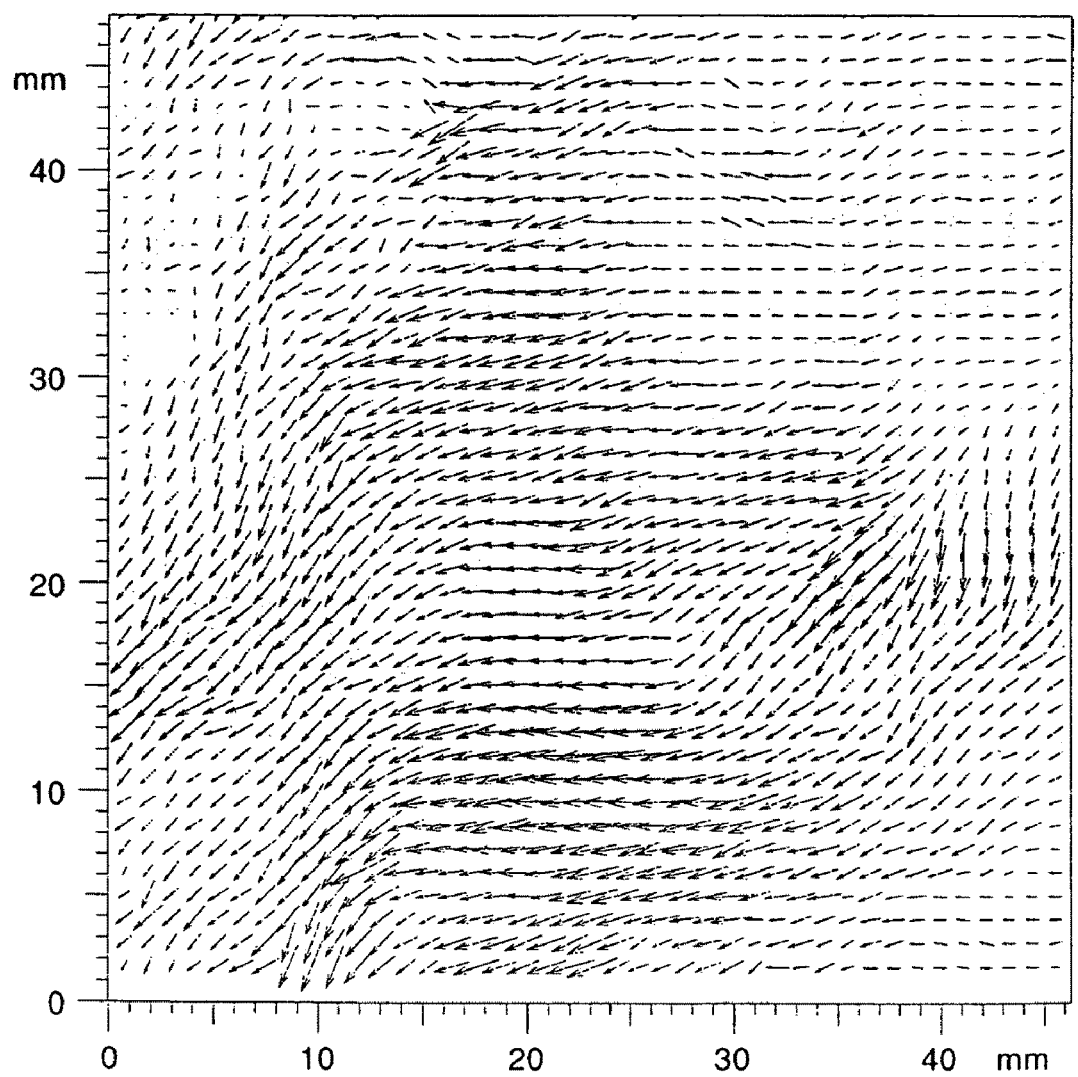
FIG. 12 is a water flow vector diagram likewise obtained with Sample L as seed particles.
Figure 13:
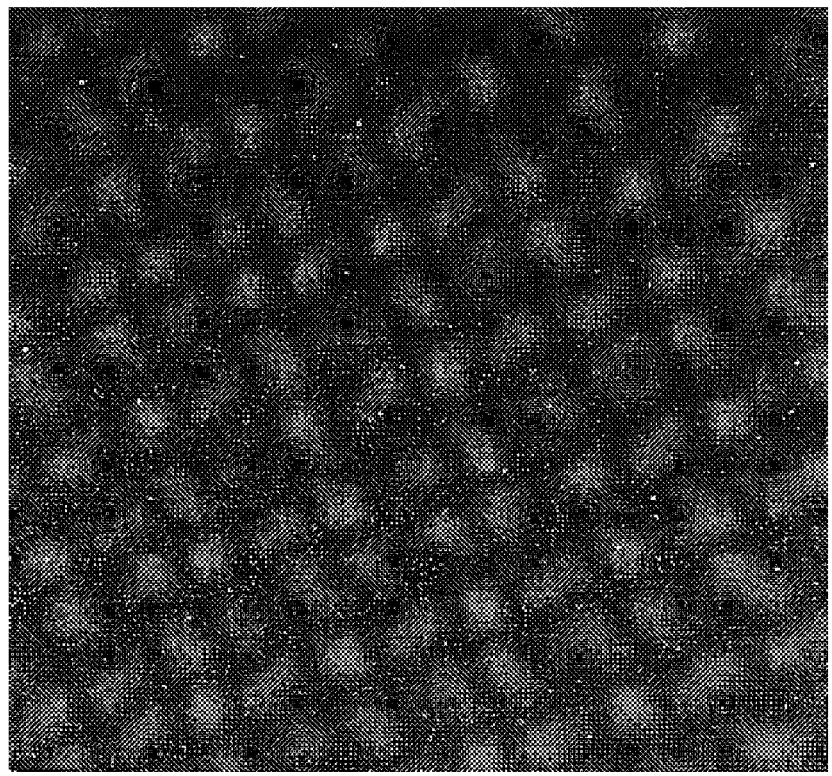
FIG. 13 is a light scattering image picture obtained with Comparative Sample (commercially available silica glass beads) as seed particles.
Figure 14:
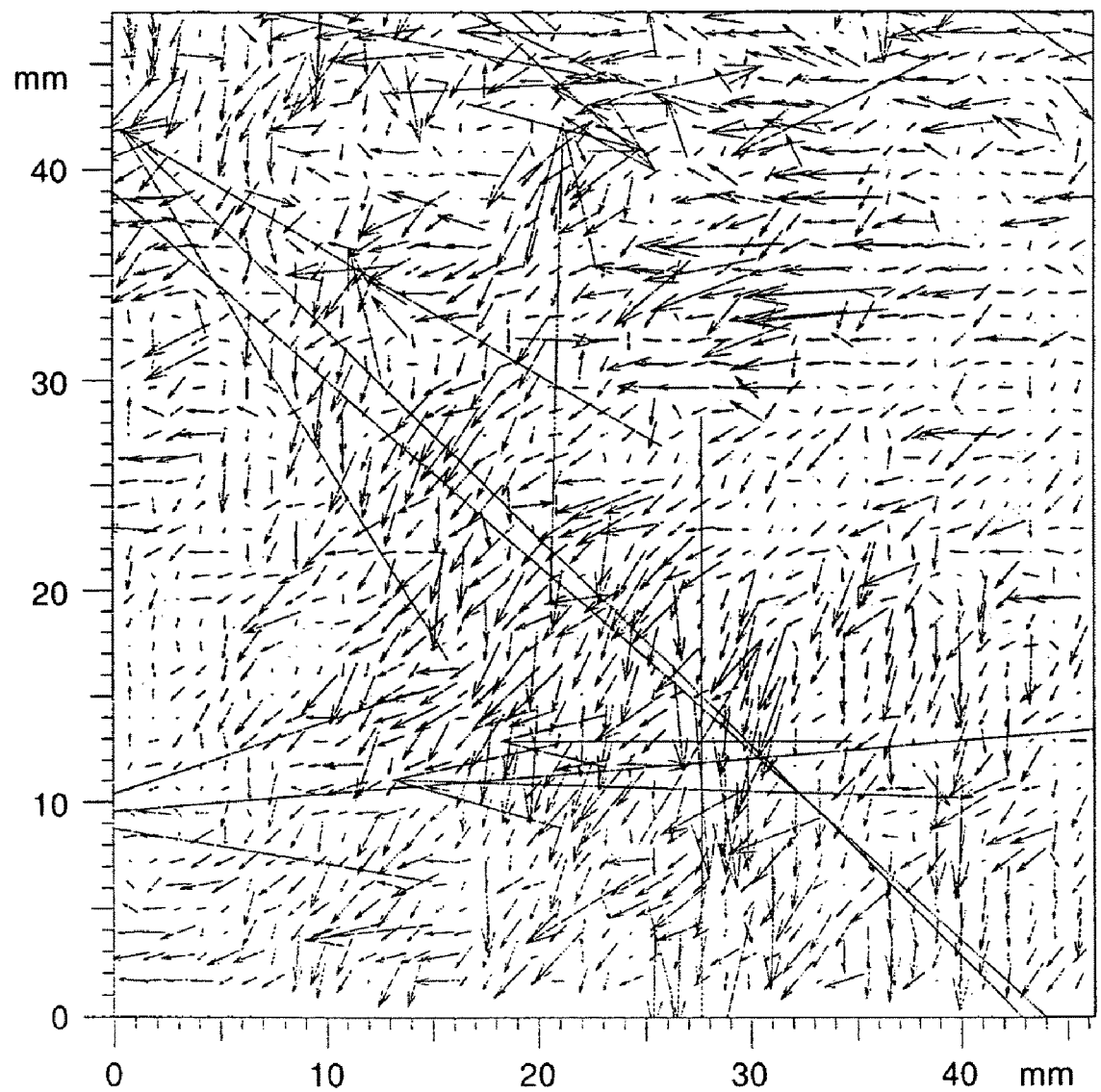
FIG. 14 is a water flow vector diagram likewise obtained with Comparative Sample (commercially available silica glass beads) as seed particles.

Sample L and commercially available silica glass beads (average particle size: 20 μm; average thickness : 1 μm) for seed particles as Comparative Sample were subjected to a water flow measurement test in a cubic water tank, using a particle image velocimeter, Model Flow Map (made by Dantec Co.). 800 cm³ of water was put into a transparent cubic water tank, 10 cm×10 cm×10 cm, and 0.01 g of Sample L or the commercially available silica beads for seed particles was added thereto as seed particles, followed by stirring with a magnetic stirrer. The water tank was irradiated with YAG pulse laser from the overhead position, while scattered light images of particles as viewed from the side of the water tank were read by a CCD camera at intervals of 0.1 μ second, followed by image processing to calculate water flow vectors as viewed from the side of the water tank. Scattered light image picture and calculated water flow vector diagram in case of using Sample L are shown in FIG. 11 and FIG. 12, respectively. Scattered light image picture and calculated water flow vector diagram in case of using the silica beads as Comparative Sample are shown in FIG. 13 and FIG. 14, respectively. In the measurement using Comparative Sample seed particles, the scattered light image was not clear and the water flow vectors were disturbed. Such disturbances never occur in the ordinary liquid flow field, and thus it was found that the accurate flow measurement was not carried out. In the measurement using Sample L seed particles, on the other hand, the scattered light image of particles was clear, and the water flow vector arrangement was in a smooth stream-line profile, showing that the accurate measurement was carried out. That is, the present fine hollow powder was found useful for accurate flow measurement as seed particles with a distinguished light scatterbility.

INDUSTRIAL APPLICABILITY

The present fine hollow powder and the thin flaky titanium oxide powder obtained according to the present invention have a distinguished dispersibility and are useful for additives to pigments, paints, cosmetics, coating materials, resins such as nylon, etc., white paper, photofunctional materials such as catalyst, etc. and ultraviolet shielding materials.

Furthermore, the present novel mixed alkali metal titanate, layered titanic acid compound and exfoliated titania sol are useful for the commercially advantageous production of said fine powder.

The invention claimed is:

1. A mixed alkali metal titanate in an orthorhombic layer structure represented by the following composition formula:

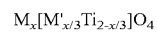

$M_x[M'_{x/3}Ti_{2-x/3}]O_4$ where M is Rb or Cs and M' is Li and x is 0.50-1.0.

2. A mixed alkali metal titanate according to claim 1, wherein said alkali metal titantate includes a space group and said space group is Immm.

3. A process for preparing a mixed alkali metal titanate comprising:

mixing alkali metal oxides $M_2O$ and $M'_2O$, where M is Rb or Cs and M' is Li, or compounds decomposable to $M_2O$ and $M'_2O$, respectively, by heating with titanium dioxide or a compound capable of forming titanium dioxide by heating in a molar ratio of M/M'/Ti of 3/1/5-3/1/11; and firing the mixture at a temperature of 500-1,100° C.

* * * * *